United States Patent [19]

Forster et al.

[11] 4,182,957
[45] Jan. 8, 1980

[54] PROCESS FOR DETERMINING THE FUEL FLOW INTO THE GASIFIER OF A PARTIAL OXIDATION INSTALLATION FOR SOLID, FINE-GRAIN OR DUST-LIKE FUELS

[75] Inventors: Manfred Forster, Essen; Ulrich Geidis, Waltrop, both of Fed. Rep. of Germany

[73] Assignee: Krupp-Koppers GmbH, Essen, Fed. Rep. of Germany

[21] Appl. No.: 829,814

[22] Filed: Sep. 1, 1977

[30] Foreign Application Priority Data

Sep. 22, 1976 [DE] Fed. Rep. of Germany ....... 2642537

[51] Int. Cl.² .............................................. G01F 1/00
[52] U.S. Cl. .................................. 250/356; 250/308; 250/359; 250/435
[58] Field of Search ................... 250/308, 356, 358 R, 250/359, 360, 432 R, 433, 435

[56] References Cited

U.S. PATENT DOCUMENTS

| | | | |
|---|---|---|---|
| 3,278,747 | 10/1966 | Ohmart | 250/359 |
| 3,280,328 | 10/1966 | Giesking | 250/359 |
| 3,604,928 | 9/1971 | Starnes | 250/359 |
| 4,044,259 | 8/1977 | Wyton et al. | 250/359 |

*Primary Examiner*—Davis L. Willis
*Attorney, Agent, or Firm*—Michael J. Striker

[57] ABSTRACT

The fuel flow into the gasifier of a partial oxidation installation using solid fine-grain or dust-like fuel is determined by a radiometric density measurement of the fuel immediately prior to its entry into the gasifier and while the fuel particles are suspended in a gaseous or vaporous medium.

10 Claims, 1 Drawing Figure

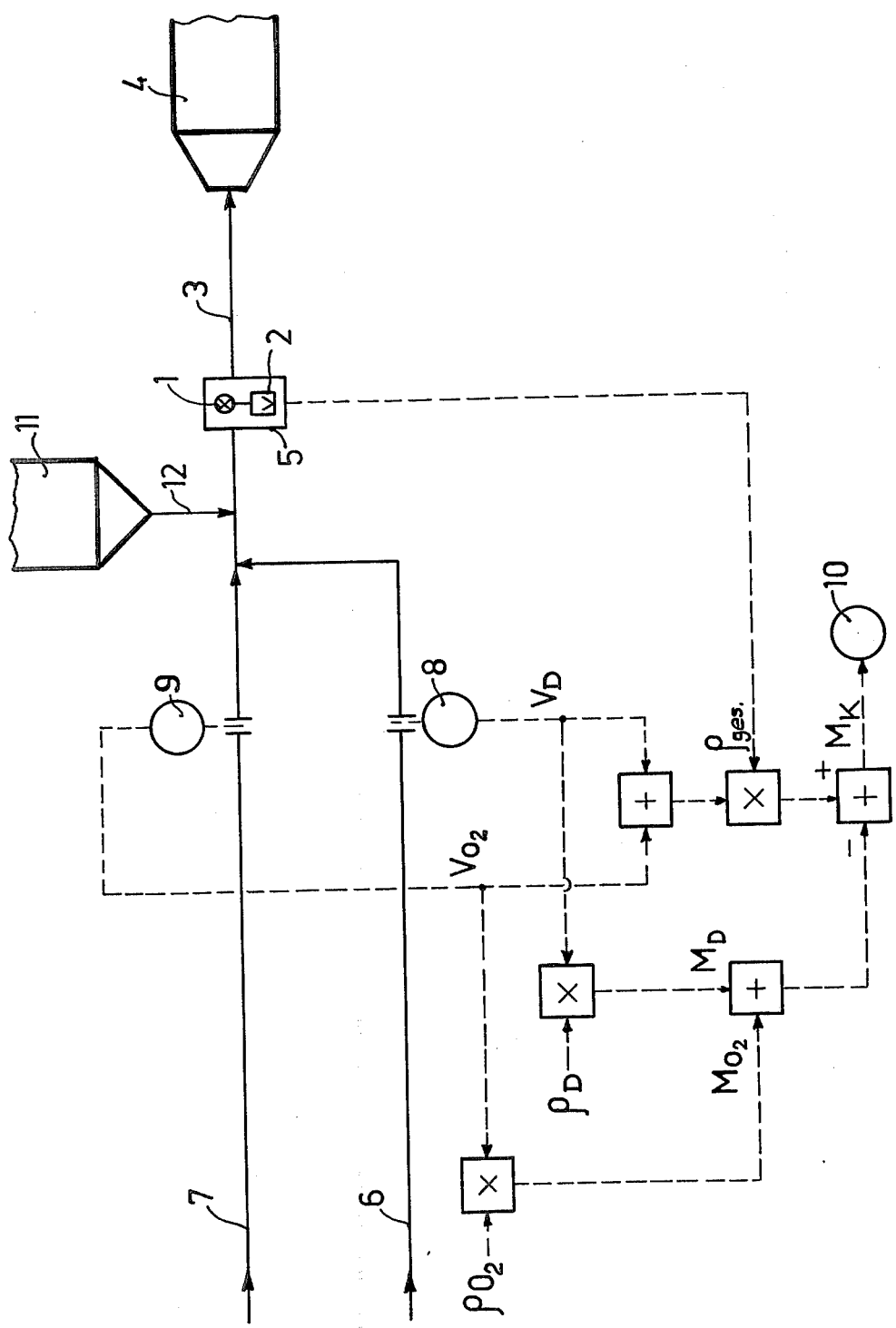

PROCESS FOR DETERMINING THE FUEL FLOW INTO THE GASIFIER OF A PARTIAL OXIDATION INSTALLATION FOR SOLID, FINE-GRAIN OR DUST-LIKE FUELS

BACKGROUND OF THE INVENTION

The present invention relates to a process for determining the fuel flow into the gasifier occurring in the partial oxidation of solid fuels of fine grained and up to dust-like particle sizes.

In the partial oxidation of solid fuels such as lignite or coal or petroleum coke it is necessary to introduce the fine-grain or dust-like fuels together with the gaseous or vaporous reaction medium in a uniform and quantitatively exactly defined flow into the gasifier. The fuel particles may be reduced to the desired grain size by means of a preceding grinding device. The uniformity and exact control of the flow to the gasifier is necessary in order to obtain constant operating conditions in the gasifier which assure a uniform quality of the produced partial oxidation gas. The gaseous or vaporous reaction media used in these cases may be oxygen or air or oxygen-enriched air and possibly also steam. If the proportion of fuel in the reaction mixture in the gasifier is too low an undesirable increase in the operating temperature in the gasifier will occur because of too high a ratio of oxygen to fuel. On the other hand if the proportion of fuel in the reaction mixture for the gasifier is too high an unstable reaction of the fuel with the oxidizing agent will result. This may have the consequence that unreacted fuel particles become deposited in the gasifier or are passed out of the gasifier together with the generated gas. Besides, it is not impossible that a breakdown of the reaction occurs.

The volume flow of the gaseous or vaporous reaction medium into the gasifier can be determined in a comparatively easy and unproblematic manner by measurement of the effective pressure differential, for instance by way of gauge orifices.

Much more difficult, however, is the quantitative determination of the solid fuels. For instance, the so-called conveyor-type scales cannot be used since fine-grained and even dust-like solid fuels cannot readily be moved onto the conveyor lines and thus be subjected to measurements.

Likewise unfeasible are measuring methods which operate by the principle of a medium flowing onto a surface or which are based on the measurement of the impact energy of a stream of solid particles onto a movable bounce plate where the impact is obtained by a constant drop height. These methods are of questionable value in the present case because of the strongly erosive properties of the fine grained or dust-like solid fuels.

In the prior art the fuel was therefore usually introduced into the gasifier by means of a screw conveyor. This means that the quantitative dosage of the fuel was largely effected by regulating the rpm of the screw conveyor. This method, however, also has an inherent lack of exactness since the physical properties of the fuel, in particular its flow behavior and adhesion property, are subject to certain changes. This method in addition requires obviously the use of a screw conveyor. This is undesirable in present methods where the conveyance of the fuel to the gasifier is effected otherwise, for instance by pneumatic conveyance.

An attempt has also been made to determine the fuel prior to its entry into the gasifier by controlling and measuring the so-called blow pressure in the inlet duct of the gasifier, that is, measuring the flow-dependent pressure of the combined reaction media (gaseous or vaporous reaction medium plus fuel). This blow pressure is composed of the flow-dependent pressure loss within the inlet duct and the back pressure of the flame, in which case the latter constitutes a substantial fraction of the blow pressure. For this reason a sudden breakdown of the reaction, that is of the flame in the gasifier, causes immediately a corresponding drop of the blow pressure. There is also the point that the pressure within the gasifier is different upon commencement of the operation than during continuous operation. In case of the initial operation the blow pressure cannot be used to control the installation. This method therefore likewise cannot be considered as desirable.

The present invention, therefore, has the object to provide for a process for determining the fuel flow into the gasifier in case of the partial oxidation (gasification) of fine-grain or dust-like solid fuels and provide such method while avoiding the shortcomings of the prior art processes.

SUMMARY OF THE INVENTION

This object is accomplished by effecting the determination of the fuel flow by a radiometric density measurement of the fuel immediately prior to its entry into the gasifier and while the fuel particles are suspended in the gaseous or vaporous medium. The method of the radiometric density measurement is known as such and has, for instance, been described in the publication "Elektroanzeiger," 1974, No. 7, pages 132–134. The radiation penetrates, along a predetermined length of flow path, the fuel which is suspended in the gaseous or vaporous reaction media and is thus weakened or decreased in proportion to the mass of irradiated fuel (density times irradiated volume of flow path). The residual radiation is then measured in a radiation detector and converted into a direct current signal which is proportional to the density.

The measuring device itself is constituted by a radioactive source of radiation which is disposed on one side of the measured flow path within a duct through which the solid fuel flows and secondly a radiation detector which is disposed opposite of the source of radiation on the other side of the flow path.

The process has the following advantages:

[1] high degree of reliability,

[2] a measurement without direct physical contact, and

[3] exact measurements both during continuing operation and during commencement of the operation.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWING

The drawing illustrates a circuit diagram of a measuring device for carrying out the process of the invention.

DESCRIPTION OF THE PREFERRED EMBODIMENT

With reference to the drawing it will be noted that 1 is a radioactive source of radiation, for instance consisting of a cesium-137 isotope and a radiation detector 2 which are arranged on opposite sides of the inlet duct 3 for the reaction mixture immediately prior to the inlet into the gasifier 4. The measuring device is surrounded by a radiation protective jacket or container 5. It will be understood that the radioactive source 1 of radiation as well as the radiation detector 2 are conventional devices which are commercially available.

The fuel is fed from the storage bin 11 via a line 12 into the inlet duct 3 and is there combined with steam from the duct 6 and oxygen from the duct 7.

By means of the radiometric density measurement there is determined the density $\rho_{total}$ of the solid fine-grain or dust-like fuel and the gaseous and vaporous reaction media which make up the reaction mixture which flows through the inlet duct 3.

In a further embodiment the process of the invention can be expanded by determining the volume flow $V_D$ of the steam which flows through the duct 6 as well as the volume flow $V_{O2}$ of the oxygen flowing through the duct 7 or air or oxygen-enriched air. This determination is effected by measuring devices (gauge orifices) 8 and 9. As indicated by the broken lines the thus-obtained measurements as well as the value $\rho_{total}$ obtained in the radiometric density measurements are then fed into a computer as indicated in the diagram.

There then exists the following mathematical relationships:

The total flow volume $V_{total}$ is composed as follows:

$$V_{total} \approx V_D + V_{O2}.$$

The volume flow of the fuel in this case can be disregarded since at a charge of for instance 2 kg/m³ it amounts only to 1 percent by volume.

The total flow mass $M_{total}$ is then composed as follows:

$$M_{total} = \rho_{total} \cdot V_{total}.$$

The fuel flow mass $M_K$ is composed as follows $$M_K = (\rho_{total} \cdot V_{total}) - (M_{O2} + M_D).$$

Considering that the flow mass $M_{O2}$ for the oxygen or the air or oxygen-enriched air is composed as follows $$M_{O2} = \rho_{O2} \cdot V_{O2}$$

and that the flow mass $M_D$ for the steam is composed as follows $$M_D = \rho_D + V_D,$$

there follows the following relationship for the fuel-gas flow mass $M_K$:

$$M_K = \rho_{total}(V_D + V_{O2}) - [(\rho_{O2} \cdot V_{O2}) + (\rho_D \cdot V_D)].$$

The densities $\rho_{O2}$ and $\rho_D$ are assumed, when fed into the computer, to be constant factors. The solution of the problem is then obtained by a computer setup as indicated diagrammatically in the drawing and using conventional electronic or pneumatic structure elements.

The obtained $M_K$-value is transmitted to the control device 10 which controls the safety interlock of the gasifier 4.

In conclusion it may be pointed out that the process of the invention does not depend on the use of specific process conditions in the partial oxidation operation. The process is applicable to widely different conditions, for instance regarding pressure, temperature reaction media, etc. The process of the invention is of course also applicable where similar conditions exist in the reaction space for the feeding of the fuel as exist in the partial oxidation. An example of such operation would be the preheating of coal.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A process for determining the fuel flow into the gasifier of a partial oxidation installation employing fine grained or dust-like solid fuels, which comprises passing the suspended fuel particles between a radioactive source of radiation and a means for detecting radiation, thereby causing a decrease in transmitted radiation, thereby causing a decrease in transmitted radiation; and determining the fuel density from the residual transmitted radiation.

2. A process according to claim 1 wherein the source of radiation is disposed within a confined zone covering a predetermined length of fuel flow path and wherein the radiation detector is disposed on the opposite side of the flow path and opposite said source of radiation.

3. A process for determining the fuel flow into the gasifier of a partial oxidation installation employing fine grained or dust-like solid fuels, which comprises subjecting the suspended fuel particles to radiation from a radioactive source throughout a predetermined length of flow path so as to cause a decrease in the transmitted radiation; recording the residual transmitted radiation by a radiation detector; and determining the fuel density from the residual transmitted radiation.

4. The process of claim 3, wherein the determination of fuel density from the residual transmitted radiation is effected by converting the measurement obtained by said radiation detector into an electrical signal which is directly proportional to the fuel density.

5. A process for determining the fuel flow into the gasifier of a partial oxidation installation employing fine grained or dust-like solid fuels in a gaseous or vaporous reaction medium consisting essentially of steam and oxygen, which comprises passing the suspended fuel particles between a radioactive source of radiation and a means for detecting said radiation, thereby causing a decrease in the transmitted radiation; determining the flow volume of the supplied reaction medium; recording the residual transmitted radiation by a radiation detector; determining the fuel density from the residual transmitted radiation; and feeding data of said flow volume and fuel density into a computer where said data is caused to generate a signal for the fuel supply based upon the mathematical relationship $$M_K = \rho_{total}(V_D + V_{O2}) - [(\rho_{O2} \cdot V_{O2}) + (\rho_D \cdot V_D)].$$

wherein
- $M_K$ = fuel flow mass
- $\rho_{total}$ = total density of the flow mass
- $V_D$ = volume of steam
- $V_{O_2}$ = volume of oxygen
- $\rho_D$ = density of steam
- $\rho_{O_2}$ = density of oxygen.

6. The process of claim 5, wherein said determination of flow volume of said reaction medium is accomplished through the pressure-differential method.

7. The process of claim 5, wherein said suspended fuel particles are passed through an inlet duct, and said determination of flow volume is made in said inlet duct.

8. The process of claim 5, wherein said determination of flow volume is effected by orifice gauges.

9. An installation for measuring the fuel supply to a gasifier for the partial oxidation of a solid finely divided or dust-like fuel, said installation comprising
- a gasifier;
- an inlet duct to said gasifier;
- means for passing said fuel and passing a fluid reaction medium into said inlet duct;
- a radioactive source of radiation disposed to one side of said inlet duct;
- a radiation detector disposed opposite said source of radiation on the other side of said inlet duct for measuring the drop in radiation caused by passing of said radiation through the particles of said fuel;
- a protective cover for said source of radiation and radiation detector;
- gauge means for measuring the flow volume of said reaction medium;
- and means for feeding impulses corresponding to the measurements obtained by said radiaton detector and said gauge means into a computer set-up for controlling the fuel flow into said gasifier.

10. The installation of claim 9, wherein said gauge means includes means for separately measuring the flow volume of components of said reaction medium.

* * * * *